(12) United States Patent
Lambeth et al.

(10) Patent No.: US 10,045,989 B2
(45) Date of Patent: Aug. 14, 2018

(54) QUINAZOLINE DERIVATIVES, COMPOSITIONS, AND USES RELATED THERETO

(71) Applicant: Emory University, Atlanta, GA (US)

(72) Inventors: John David Lambeth, Decatur, GA (US); Thota Ganesh, Alpharetta, GA (US); Susan M. Smith, Acworth, GA (US); Aiming Sun, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/147,531

(22) Filed: May 5, 2016

(65) Prior Publication Data

US 2016/0243121 A1 Aug. 25, 2016

Related U.S. Application Data

(62) Division of application No. 14/401,930, filed as application No. PCT/US2013/042842 on May 28, 2013, now abandoned.

(60) Provisional application No. 61/653,622, filed on May 31, 2012.

(51) Int. Cl.
| | | |
|---|---|---|
| A61K 31/517 | (2006.01) | |
| A61Q 19/08 | (2006.01) | |
| A61Q 17/04 | (2006.01) | |
| A61K 8/49 | (2006.01) | |
| C07D 403/06 | (2006.01) | |
| C07D 239/78 | (2006.01) | |
| C07D 417/12 | (2006.01) | |
| A61Q 19/00 | (2006.01) | |

(Continued)

(52) U.S. Cl.
CPC .......... *A61K 31/517* (2013.01); *A61K 8/4953* (2013.01); *A61Q 17/04* (2013.01); *A61Q 19/00* (2013.01); *A61Q 19/08* (2013.01); *C07D 239/78* (2013.01); *C07D 239/95* (2013.01); *C07D 401/06* (2013.01); *C07D 403/06* (2013.01); *C07D 417/12* (2013.01)

(58) Field of Classification Search
CPC .. C07D 401/12; A61K 31/517; A61K 31/551; A61K 31/5377
See application file for complete search history.

(56) References Cited

U.S. PATENT DOCUMENTS

| | | |
|---|---|---|
| 3,919,425 A | 11/1975 | Vidrio |
| 6,369,086 B1 | 4/2002 | Davis |
| 6,369,087 B1 | 4/2002 | Whittle |

(Continued)

FOREIGN PATENT DOCUMENTS

| | | |
|---|---|---|
| WO | 2000/034278 | 6/2000 |
| WO | 2012/058211 | 5/2012 |

OTHER PUBLICATIONS

Nawrocka et al., "Syntheses of Novel 3-Amino-2(1H)-thioxo-4(3H)-quinazolinones and Evaluation of their Immunotropic Activities. Part III", Arch. Pharm. Pharm. Med, Chem. 330, 390-405 (1997).*

(Continued)

*Primary Examiner* — Jianfeng Song
(74) *Attorney, Agent, or Firm* — Emory Patent Group

(57) ABSTRACT

The disclosure relates to quinazoline derivatives, compositions, and methods related thereto. In certain embodiments, the disclosure relates to inhibitors of NADPH-oxidases (Nox enzymes) and/or myeloperoxidase.

3 Claims, 3 Drawing Sheets

(51) Int. Cl.
  *C07D 239/95* (2006.01)
  *C07D 401/06* (2006.01)

(56) References Cited

U.S. PATENT DOCUMENTS

| | | |
|---|---|---|
| 6,372,733 B1 | 4/2002 | Caldwell |
| 6,372,778 B1 | 4/2002 | Tung |
| 2006/0229324 A1 | 10/2006 | Itai |
| 2009/0163545 A1 | 6/2009 | Goldfarb |
| 2013/0225612 A1 | 8/2013 | Lambeth |

OTHER PUBLICATIONS

Silverman, "The Organic Chemistry of Drug Design and Drug Action", p. 19-21, 1992.*

Pubchem, "Substance Record for SID 125236088", available date Sep. 12, 0111, retrieved from https://pubchem.ncbi.nlm.nih.gov/substance/125236088.*

Ettmayer et al., 2004, Lessons Learned from Marketed and Investigational Prodrugs, Journal of Medicinal Chemistry, 47 (10), 2393-2404.

Hayao, et al., 1965, New Sedative and Hypotensive 3-Substituted 2,4(1H,3H)-Quinazolinediones, J. Med. Chem., 8 (6), 807-811.

Jaquet et al., 2009, Small-Molecule NOX Inhibitors: ROS-Generating NADPH Oxidases as Therapeutic Targets, Antioxid. Redox. Signal., 11(10), 2535-2552.

Jaquet et al. NADPH oxidase (NOX) isoforms are inhibited by celastrol with a dual mode of action, British Journal of Pharmacology (2011) 164 507-520 507-520.

Li et al. Thioxo-dihydroquinazolin-one Compounds as Novel Inhibitors of Myeloperoxidase, ACS Med. Chem. Lett. 2015, 6, 1047-1052.

Malle et al., 2007, Myeloperoxidase: a target for new drug development, British Journal of Pharmacology, 152(6), 838-854.

Sheridan, R. P. 2002, The Most Common Chemical Replacements in Drug-Like Compounds, J. Chem. Inf. Comput. Sci., 42(1), 103-108.

Tiden et al., 2011, 2-Thioxanthines Are Mechanism-based Inactivators of Myeloperoxidase That Block Oxidative Stress during Inflammation, J. Biol. Chem., 286, 37578-37589.

Smith et al. Ebselen and congeners inhibit NADPH oxidase 2-dependent superoxide generation by interrupting the binding of regulatory subunits. Chem Biol. 2012,19(6):752-63.

* cited by examiner

QUINAZOLINE DERIVATIVES, COMPOSITIONS, AND USES RELATED THERETO

CROSS REFERENCE TO RELATED APPLICATIONS

This application is a division of U.S. patent application Ser. No. 14/401,930 filed Nov. 18, 2014, which is the National Stage if International Application Number PCT/US2013/042842 filed May 28, 2013, which claims the benefit of priority to U.S. Provisional Application No. 61/653,622 filed May 31, 2012. The entirety of each of these applications is hereby incorporated by reference for all purposes.

STATEMENT REGARDING FEDERALLY SPONSORED RESEARCH OR DEVELOPMENT

This invention was made with Government Support under Grant No. 3R01CA084138-08S1 awarded by the National Institutes of Health. The Government has certain rights in the invention.

FIELD

The disclosure relates to quinazoline derivatives, compositions, and methods related thereto. In certain embodiments, the disclosure relates to inhibitors of NADPH-oxidases (Nox enzymes) and/or myeloperoxidase (MPO).

BACKGROUND

The Nox enzymes represent a family of membrane enzymes (Nox1, Nox2, Nox3, Nox4, Nox5, Duox1 and Duox2) that catalyze NADPH-dependent generation of superoxide and/or hydrogen peroxide. These reactive oxygen species (ROS) can be further metabolized to other reactive products such as hypochlorous acide (HOCl) and peroxinitrite (HOONO). While the Nox enzymes have normal biological functions in signal transduction and host defense, they have also been implicated in the pathogenesis of a variety of diseases. Nox inhibitors and myeloperoxidase inhibitors have therapeutic uses and uses in biological assays. See Jaquet et al., 2009. Antioxid Redox Signal. 11(10):2535-52 and Malle et al., 2007, British Journal of Pharmacology 152(6):838-854.

The core catalytic domain of NOX enzymes share similar structure. The Nox enzymes' only known biochemical function is the generation of reactive oxygen species (ROS). The basic catalytic subunit of NOX contains a C-terminal dehydrogenase domain featuring a binding site for NADPH and bound flavin adenine nucleotide (FAD), as well as an N-terminal domain consisting of six trans-membrane helices that bind two heme groups. Upon enzyme activation, NADPH transfers its electron to the FAD, which in turn passes electrons sequentially to two hemes and ultimately to molecular oxygen to produce superoxide ($O_2$—) and/or hydrogen peroxide ($H_2O_2$), depending upon the isoform. Although NOX-isoforms all catalyze the reduction of the molecular oxygen, they differ in their tissue distribution, their subunit requirement, domain structure, and mechanism by which they are activated. Depending upon the clinical condition, either isoform-selective, or Nox/Duox pan-specific inhibitors are contemplated to be useful for therapeutic applications. Potential Nox inhibitors have been investigated, such as diphenylene iodonium (DPI), apocynin, VAS2870, and pyrazolopyridines. There exists a need to identify inhibitors for Nox enzymes.

Much of the cell damage that arises from ROS is a result of further metabolism of the ROS to more reactive molecules. The ROS produced by Nox enzymes includes hydrogen peroxide, which is a substrate for the enzyme Myeloperoxidase (MPO. MPO catalyzes the reaction of hydrogen peroxide with a halide (e.g. chloride) to form a hypohalous acids (e.g., hypochlorite), or can react to oxidize a variety of other small molecules. MPO is implicated in causing a variety of oxidations and modifications of proteins, lipids and nucleic acids, and is thought to be a major form of ROS that causes cell damage and inflammation in a variety of diseases. MPO is expressed in neutrophils, macrophages and other cell types such as microglia where it plays a pathogenic role in disease states especially those involving inflammation. Both Nox enzymes and MPO are implicated in a wide range of diseases including acute lung inflammation, COPD, cystic fibrosis, Alzheimer's Disease, Parkinson's Disease, pulmonary hypertension, stroke, schizophrenia, traumatic brain injury, asbestos lung injury, multiple sclerosis, myocardial infarction, atherosclerosis, chronic heart failure, inflammatory bowel disease, asthma, cancer, and others. Thus MPO inhibitors are contemplated to be useful for therapeutic applications. Malle, et al. 2007 British Journal Pharmacology 152:838-854; Tiden et al. 2011. Journal of Biological Chemistry 286:37578-37589.

Certain quinazoline derivatives were identified in references. Hayao et al., J Med Chem 1965, 8:6, 807-11 disclose quinazoline derivatives produce vasodilation. See also U.S. Pat. No. 3,919,425. International PCT App. No. WO 2000/034278 discloses triazolo derivatives as chemokine inhibitors. US Patent App. No. 2009/0163545 discloses compounds for altering the lifespan of a eukaryotic organism identified using a DeaD assay.

References cited herein are not an admission of prior art.

SUMMARY

It has been discovered that certain compounds inhibit Nox enzymes and/or MPO, depending upon structural variations. In some embodiments, the disclosure relates to compounds and methods of treating or preventing a NOX- and/or MPO-related disease comprising administering to a subject a pharmaceutical composition comprising a 2-thioxo-2,3-dihydroquinazolin-4-one derivative such as those of formula I,

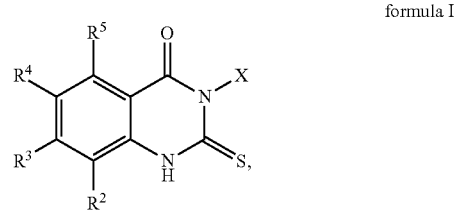

formula I or pharmaceutically acceptable salt or prodrug thereof, wherein;

X is —$(CR^{14}R^{15})_n$—Y, —$NH(CR^{14}R^{15})_n$—Y, or $NH_2$ optionally substituted with one or more, the same or different, $R^{10}$;

n is 1, 2, 3, 4, 5, or 6;

Y is hydrogen, alkyl, or an aromatic heterocyclcyl such as pyridinyl or imidazoliyl optionally substituted with one or more, the same or different, $R^{10}$;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{10}$;

$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{10}$;

$R^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{10}$; or $R^3$ and $R^4$ form a heterocyclic ring;

$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{14}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{16}$;

$R^{15}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In some embodiments, the disclosure relates to compounds and methods of treating or preventing a NOX related disease comprising administering to a subject a pharmaceutical composition comprising a 2-alkylquinazolin-4(3H)-one derivative such as those of formula II

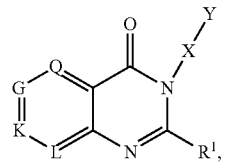

formula II or pharmaceutically acceptable salt or prodrug thereof, wherein;

Q is N or C—$R^5$;
G is N or C—$R^4$;
K is N or C—$R^3$;
L is N or C—$R^2$;
X is -(A)$_n$-, —NH-(A)$_n$—, or —NH$_2$ where Y is absent optionally substituted with one or more, the same or different, $R^{10}$;
n is 1, 2, 3, 4, 5, 6, 7, or 8;
A is the same or different at each occurrence O, NH, S, CR$^{14}$R$^{15}$, or C=O;
Y is OR$^6$, SR$^6$, NR$^6$R$^7$, or $^+$NR$^6$R$^7$R$^{17}$;
$R^1$ is alkyl optionally substituted with one or more, the same or different, $R^{10}$;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{10}$;

$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{10}$;

$R^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{10}$;

$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{10}$;

$R^6$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{16}$;

$R^7$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^{16}$; or $R^6$ and $R^7$ and the nitrogen to which they bond form a 3 to 8 membered heterocyclyl optionally substituted with one or more, the same or different, $R^{16}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{14}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{16}$;

$R^{15}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;

$R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and $R^{17}$ is alkyl optionally substituted with one or more $R^{18}$ selected from halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the 2-thioxo-2,3-dihydroquinazolin-4-one or 2-methylquinazolin-4(3H)-one derivatives may be any compound disclosed herein optionally substituted with one or more, the same or different, substituents or salts thereof.

In certain embodiments, the disclosure relates to the use of a compound as described herein in the production of a medicament for the treatment of a NOX related disease. Compounds disclosed here can be contained in pharmaceutical compositions and administered alone or in combination with one or more additional active agents. The active agents can be administered simultaneously in the same dosage form or in separate dosage forms. Alternatively, the active agents can be administered sequentially in different dosage forms.

The compound can be combined with one or more pharmaceutically acceptable excipients to form a pharmaceutical composition. The compositions can be formulated for enteral, parenteral, topical, transdermal, or pulmonary administration. The compounds can be formulated for immediate release, controlled release, and combinations thereof. Examples of controlled release formulations include delayed release, extended release, pulsatile release, and combinations thereof.

The compounds described herein can be used to treat a variety of Nox-related diseases including, but not limited to, hypertension, chronic obstructive pulmonary disease (COPD), Alzheimer's disease (AD), Parkinson's disease (PD), acute respiratory distress syndrome (ARDS), acute lung injury (ALI), amyotrophic lateral sclerosis (ALS), atherosclerosis, aging-related deafness, inflammatory diseases, such as arthritis; various cancers such as colon cancer, prostate cancer, fibrotic diseases, such as liver fibrosis, pulmonary fibrosis, idiopathic pulmonary fibrosis, cirrhosis, endomyocardial fibrosis, mediastinal fibrosis, myelofibrosis, retroperitoneal fibrosis, nephrogenic systemic fibrosis, Crohn's disease, and scleroderma/systemic sclerosisreper, reperfusion injury-related disorders, such as myocardial infarction; ischemic stroke, preservation of organs during transplantation, ischemia/reperfusion injury (including stroke, myocardial infarction), diabetes, acute lung inflammation, cardiac hypertrophy, diabetic nephropathy, scar formation, skin aging and damage, and psoriasis.

In some embodiments, it is contemplated that compositions disclosed herein can be administered to subject before, during or after certain medical procedures, such as, organ transplants (heart, kidneys, liver, lungs, pancreas, intestine, and thymus) or other surgeries that reduce blood flow (cardiovascular surgery). The subject may be receiving or donating the organ.

In some embodiments, it is contemplated that composition disclosed herein can be used in biological (organ, tissue, or cell) storage mediums, typically aqueous solutions maintained at or below room temperatures, which may contain other ingredients such as, but not limited to, salts (sodium chloride, sodium lactate, calcium chloride, potassium chloride), amino acids, saccharides, polysaccharides (dextran, chondroitin, hydroxyethyl starch), vitamins (thiamine, ascorbic acid, calciferol, riboflavin, pyridoxine, tocopherol, cobalamins, phylloquinone, pantothenic acid, biotin, niacin, folic acid) and/or adenosine triphosphate or precursors (adenosine, inosine, and adenine).

In certain embodiments, the disclosure relates to method of making compounds disclosed herein by mixing starting materials and reagents disclosed herein under conditions such that the compounds are formed.

DETAILED DESCRIPTION

Figure 1:
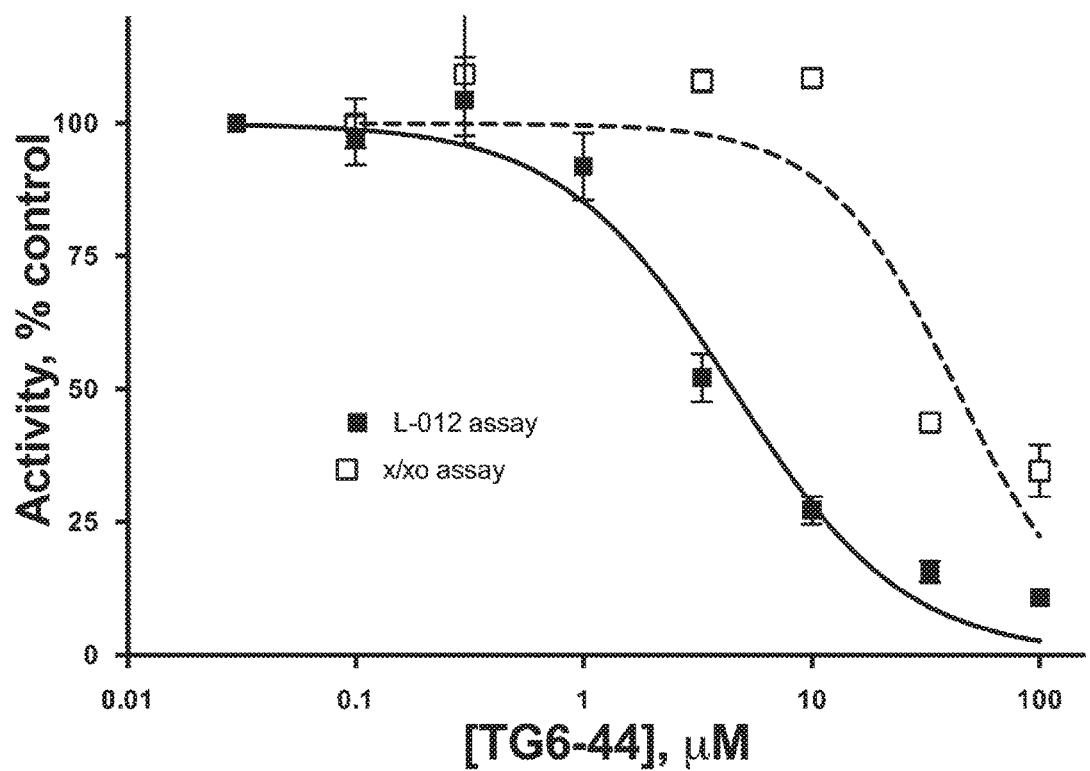
FIG. 1 shows data of the TG6-44 compound in the cell-free L-012 assay, the hydrogen peroxide-luminol assay ($H_2O_2$) and xanthine/xanthine oxidase-L-012 assay. TG6-44 Inhibits ROS activity from neutrophil membranes assayed by L-012, but does not affect control assay in which ROS is generated from xanthine plus xanthine oxidase.
Figure 2:
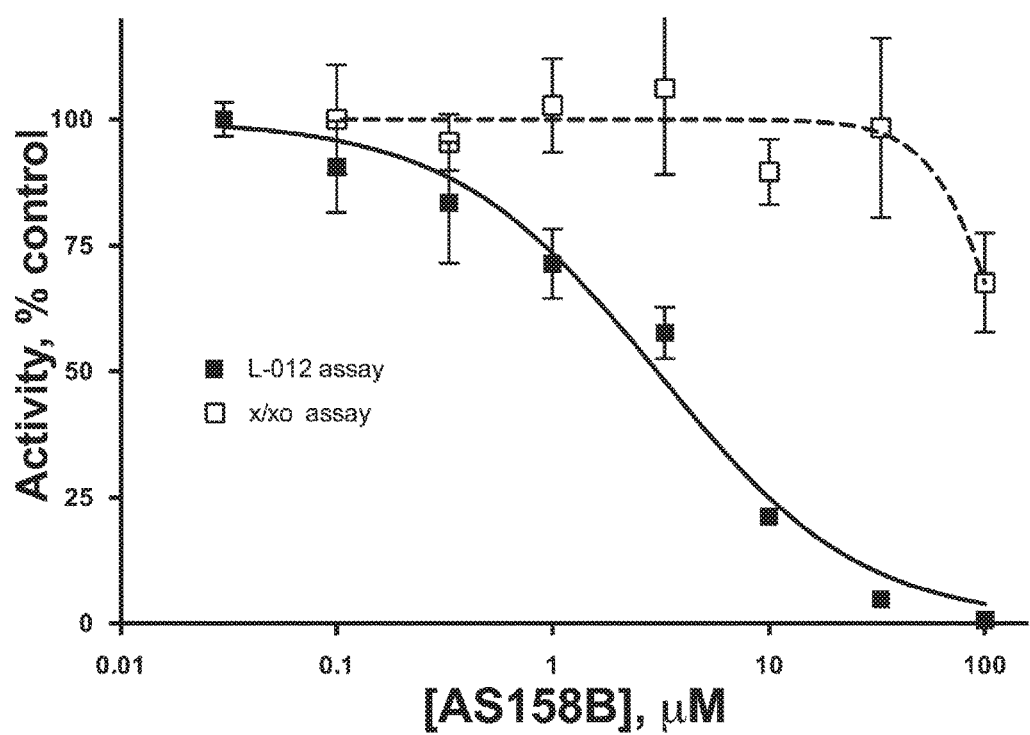
FIG. 2 shows data of the AS158b compound in the cell-free L-012 assay, the hydrogen peroxide-luminol assay ($H_2O_2$) and xanthine/xanthine oxidase-L-012 assay. AS158B inhibits ROS generation from neutrophil membranes assayed by L-012, but does not affect control assay in which ROS is supplied by xanthine oxidase.
Figure 3:
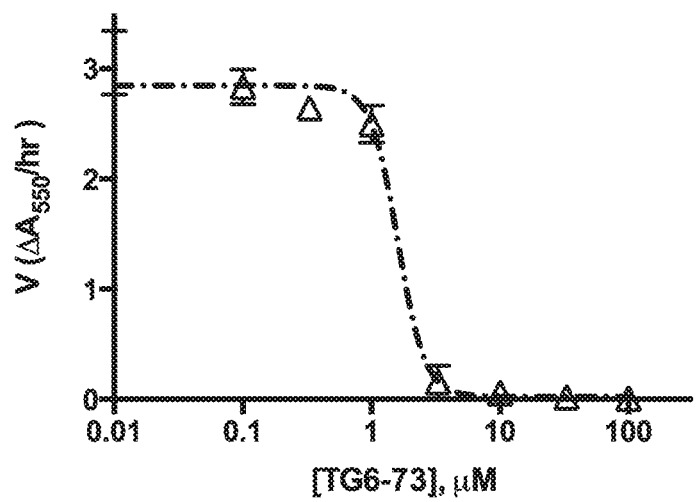
FIG. 3 shows data of the TG6-73 compound in the neutrophil cytochrome c reduction, directly demonstrating inhibition of Nox2 superoxide-generating activity. TG6-73 inhibits superoxide production from Nox2 in intact human neutrophils assayed by cytochrome c reduction monitored by absorbance increase at 550 nm.
Figure 4:
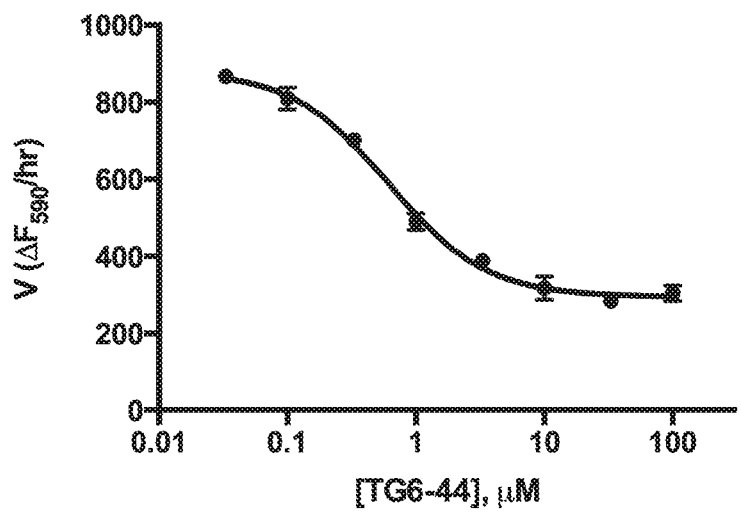
FIG. 4 shows data of the TG6-44 compound in the Amplex Red assay, directly demonstrating inhibition of MPO enzymatic activity. TG6-44 inhibits the activity of purified MPO measured by the increase in $H_2O_2$-dependent Amplex Red fluorescence.

It has been discovered that 2-thioxo-2,3-dihydroquinazolin-4(1H)-one analogs are Nox and MPO inhibitors. The disclosure relates to quinazoline derivatives, compositions, and methods related thereto. In certain embodiments, the disclosure relates to inhibitors of Myeloperoxidase and one or more NADPH-oxidases, e.g., Nox1, Nox2, Nox3, Nox4, Nox5, Duox1 and/or Duox2.

Compounds

In certain embodiments, the disclosure relates to a pharmaceutical composition comprising a compound of formula I,

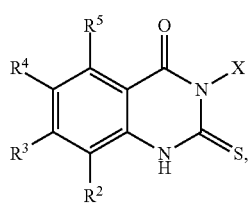

formula I or pharmaceutically acceptable salt or prodrug thereof, wherein;

X is —$(CR^{14}R^{15})_n$—Y, —$NH(CR^{14}R^{15})_n$—Y, or $NH_2$ optionally substituted with one or more, the same or different, $R^{10}$;

n is 1, 2, 3, 4, 5, or 6;

Y is hydrogen, alkyl, or an aromatic heterocyclcyl such as pyridinyl or imidazoliyl optionally substituted with one or more, the same or different, $R^{10}$;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{10}$;

$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{10}$;

$R^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{10}$; or $R^3$ and $R^4$ form a heterocyclic ring;

$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{14}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{16}$;

$R^{15}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 4.

In certain embodiments, Y is alkyl substituted with (alkyl)$_2$amino, $R^3$ is alkoxy and $R^4$ is alkoxy or $R^3$ and $R^4$ form a ring from —OCH$_2$O— or —OCH$_2$CH$_2$O—.

In certain embodiments, $R^4$ is hydrogen and $R^3$ is hydrogen.

In certain embodiments, $R^4$ is halogen and $R^3$ is hydrogen.

In certain embodiments, $R^4$ is halogen and $R^3$ is halogen.

In certain embodiments, $R^3$ is alkoxy and $R^4$ is alkoxy or $R^3$ and $R^4$ form a ring from —OCH$_2$O— or —OCH$_2$CH$_2$O—.

In certain embodiments, $R^{14}$ and $R^{15}$ are each individually hydrogen or alkyl.

In certain embodiments, the disclosure relates to a pharmaceutical composition comprising a compound of formula IA,

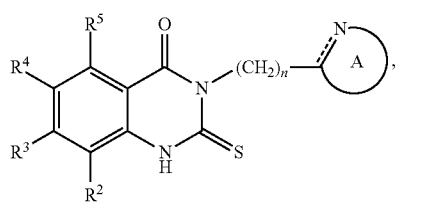

formula IA or pharmaceutically acceptable salt or prodrug thereof, wherein;

A is a five or six membered aromatic heterocyclic ring optionally substituted with one or more, the same or different, $R^{10}$; the dotted line represents a double or single bond;

n is 1, 2, 3, 4, 5, or 6;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{10}$;

$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{10}$;

$R^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{10}$; or $R^3$ and $R^4$ form a heterocyclic ring.

$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and $R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^4$ is hydrogen and $R^3$ is hydrogen.

In certain embodiments, $R^4$ is halogen and $R^3$ is hydrogen.

In certain embodiments, $R^4$ is halogen and $R^3$ is halogen.

In certain embodiments, $R^3$ is alkoxy and $R^4$ is alkoxy.

In certain embodiments, $R^3$ and $R^4$ form a ring from —OCH$_2$O— or —OCH$_2$CH$_2$O—.

In certain embodiments, $R^{14}$ and $R^{15}$ are each individually hydrogen or alkyl.

In certain embodiments, the disclosure relates to a pharmaceutical composition comprising a 2-alkylquinazolin-4 (3H)-one derivative such as those of formula II,

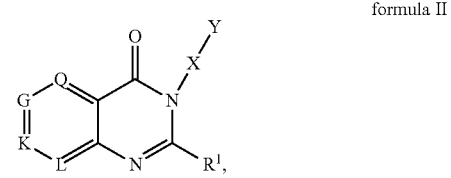

formula II or pharmaceutically acceptable salt or prodrug thereof, wherein;

Q is N or C—R⁵;
G is N or C—R⁴;
K is N or C—R³;
L is N or C—R²;
X is -(A)ₙ-, —NH-(A)ₙ-, or —NH₂ where Y is absent optionally substituted with one or more, the same or different, R¹⁰;
n is 1, 2, 3, 4, 5, 6, 7, or 8;
A is the same or different at each occurrence O, NH, S, CR¹⁴R¹⁵, or C=O;
Y is OR⁶, SR⁶, NR⁶R⁷, or ⁺NR⁶R⁷R¹⁷;
R¹ is alkyl optionally substituted with one or more, the same or different, R¹⁰;
R² is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R² is optionally substituted with one or more, the same or different, R¹⁰;
R³ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R³ is optionally substituted with one or more, the same or different, R¹⁰;
R⁴ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R⁴ is optionally substituted with one or more, the same or different, R¹⁰;
R⁵ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R⁵ is optionally substituted with one or more, the same or different, R¹⁰;
R⁶ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R⁶ is optionally substituted with one or more, the same or different, R¹⁶;
R⁷ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R⁷ is optionally substituted with one or more, the same or different, R¹⁶; or
R⁶ and R⁷ and the nitrogen to which they bond form a 3 to 8 membered heterocyclyl optionally substituted with one or more, the same or different, R¹⁶;
R¹⁰ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹⁰ is optionally substituted with one or more, the same or different, R¹¹;
R¹¹ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹¹ is optionally substituted with one or more, the same or different, R¹²;
R¹² is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹² is optionally substituted with one or more, the same or different, R¹³;
R¹³ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
R¹⁴ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹⁴ is optionally substituted with one or more, the same or different, R¹⁶;
R¹⁵ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹⁵ is optionally substituted with one or more, the same or different, R¹⁶;
R¹⁶ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and
R¹⁷ is alkyl optionally substituted with one or more R¹⁸ selected from halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, R¹ is alkyl, methyl or ethyl.

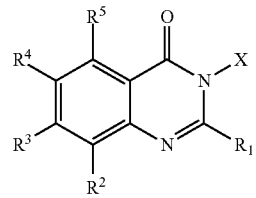

formula IIA or pharmaceutically acceptable salt or prodrug thereof, wherein;

X is —(CR$^{14}_R$$^{15}$)$_n$—Y, —NH(CR$^{14}$R$^{15}$)$_n$—Y, or NH$_2$ optionally substituted with one or more, the same or different, R$^{10}$;

n is 1, 2, 3, 4, 5, or 6;

Y is hydrogen, alkyl, or an aromatic heterocyclcyl such as pyridinyl or imidazoliyl optionally substituted with one or more, the same or different, R$^{10}$;

R$^1$ is alkyl optionally substituted with one or more, the same or different, R$^{10}$;

R$^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^2$ is optionally substituted with one or more, the same or different, R$^{10}$;

R$^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^3$ is optionally substituted with one or more, the same or different, R$^{10}$;

R$^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^4$ is optionally substituted with one or more, the same or different, R$^{10}$; or R$^3$ and R$^4$ form a heterocyclic ring;

R$^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^5$ is optionally substituted with one or more, the same or different, R$^{10}$;

R$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{10}$ is optionally substituted with one or more, the same or different, R$^{11}$;

R$^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{11}$ is optionally substituted with one or more, the same or different, R$^{12}$;

R$^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{12}$ is optionally substituted with one or more, the same or different, R$^{13}$;

R$^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

R$^{14}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{14}$ is optionally substituted with one or more, the same or different, R$^{16}$;

R$^{15}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{15}$ is optionally substituted with one or more, the same or different, R$^{16}$; and R$^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to a pharmaceutical composition comprising a compound of formula IIB,

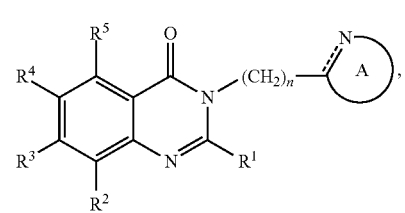

formula IIB or pharmaceutically acceptable salt or prodrug thereof, wherein;

A is a five or six membered aromatic heterocyclic ring optionally substituted with one or more, the same or different, R$^{10}$; the dotted line represents a double or single bond;

n is 1, 2, 3, 4, 5, or 6;

R$^1$ is alkyl optionally substituted with one or more, the same or different, R$^{10}$;

R$^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^2$ is optionally substituted with one or more, the same or different, R$^{10}$;

R$^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^3$ is optionally substituted with one or more, the same or different, R$^{10}$;

R$^4$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^4$ is optionally substituted with one or more, the same or different, R$^{10}$; or R$^3$ and R$^4$ form a heterocyclic ring.

R$^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and $R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^4$ is hydrogen and $R^3$ is hydrogen.

In certain embodiments, $R^4$ is halogen and $R^3$ is hydrogen.

In certain embodiments, $R^4$ is halogen and $R^3$ is halogen.

In certain embodiments, $R^3$ is alkoxy and $R^4$ is alkoxy.

In certain embodiments, $R^3$ and $R^4$ form a ring from —OCH$_2$O— or —OCH$_2$CH$_2$O—.

In certain embodiments, $R^{14}$ and $R^{15}$ are each individually hydrogen or alkyl.

Compound Activity

The following compounds were tested according to the procedures provided in the experimental section. Assays were carried out using the Nox2 cell-free system, or using purified, isolated myeloperoxidase in a standard activity assay that monitors oxidation of Amplex Red. The IC$_{50}$ value is the concentration giving half-maximal inhibition, while the "% inhibition" shown in parentheses is the maximum inhibition achieved at a high concentration of the compound. 100% refers to complete inhibition within experimental error of the assay.

In Table 1 a cell-free semi-recombinant system (consisting of isolated plasma membranes from human neutrophils as a source for Nox2-p22phox and MPO), supplemented with recombinant p47phox, p67phox and Rac1Q61L (activated Rac), expressed in and isolated from of *E. coli*. L-012 luminescence was used as a readout to monitor enzymatic activity that monitors the combined enzymatic activity of both the Nox2 system and MPO. The L-012 assay does not distinguish between inhibition of Nox2 and inhibition of MPO.

TABLE 1

Compounds that inhibit in L-012 cell-free assay of Nox/MPO activity.

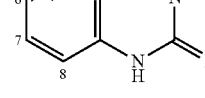

| Entry | R | $R_1$ | X | L-012 Assay IC$_{50}$, μM ± SEM |
|---|---|---|---|---|
| 2a | 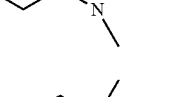 | H | S | 3.3 ± 0.3 |
| 2b | 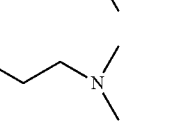 | H | O | N.I |
| 2c (TG6-44) | 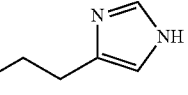 | 6-Cl | S | 1.2 ± 0.1 |
| 2zz | 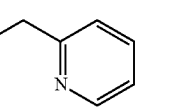 | H | S | 1 ± 0.3 |
| 2zzz | | H | S | 4 ± 1 |
| | —(CH$_2$)$_4$N(CH$_3$)$_2$ | 6-7-OMe | S | 1 |
| 3k | CH$_2$CH$_3$ | 6-F | S | 0.7 ± 0.1 |
| 3l | CH(CH$_3$)$_2$ | 6,7-F | S | 0.7 ± 0.1 |
| 3m | CH(CH$_3$)$_2$ | 6-7-OMe | S | 0.7 ± 0.1 |

In Table 2, isolated, purified human Myeloperoxidase was used in an enzyme assay system including hydrogen peroxide as substrate and Amplex Red to measure MPO enzymatic activity. These data provide examples of compounds that directly inhibit MPO.

TABLE 2

Compounds that inhibit MPO activity using the Amplex Red Assay.

| Compound | R | $R_1$ | X | IC$_{50}$ (μM) Amplex Red |
|---|---|---|---|---|
| TG6-44 | | 6-Cl | S | 1 |
| TG6-250 | | 6,7-F | S | 1 |

TABLE 2-continued

Compounds that inhibit MPO activity using the Amplex Red Assay.

| Compound | R | R₁ | X | IC$_{50}$ (μM) Amplex Red |
|---|---|---|---|---|
| LY1-27 | (propyl-imidazole) | N | S | 1 |
| LY1-107N | (propyl-4-methylpiperazine) | 6-F | S | 1 |
| TG6-17-2 | (propyl-N,N-dimethylamine) | H | S | 1.5 |
| TG6-52-2 | (propyl-pyrrolidine) | H | S | 1.5 |
| LY2-43 | (methyl-piperidine) | 6-F | S | 0.5 |
| TG6-27-2 | (propyl-N,N-diethylamine) | H | S | 2 |
| TG6-52 | (propyl-pyrrolidine) HCl | H | S | 1.5 |
| TG6-248 | (propyl-N,N-dimethylamine) HCl | 6-F | S | 2 |
| LY1-23 | (propyl-2-pyridine) HCl | H | S | 2 |
| LY1-73 | (propyl-imidazole) HCl | 6-F | S | 1.5 |
| AS261b | NH₂ | 7-CO₂Me | S | 1.5 |
| LY1-21 | (propyl-OMe) | H | S | 3 |
| LY1-31 | (isobutyl-OMe) | H | S | 2.5 |
| AS2-30 | (butyl-N,N-dimethylamine) HCl | 6,7-OMe | S | 4 |

Isolated human neutrophils represent a system in which superoxide originates from the endogenous Nox2 enzyme system, and can be measured using cytochrome c reduction that is inhibitable by added superoxide dismutase. In Table 3, Nox2 activity in isolated human neutrophils was assayed using cytochrome c reduction. These data provide examples of compounds that directly inhibit the Nox2 enzyme system.

TABLE 3

Compounds that inhibit Nox2, assayed by cytochrome c reduction in activated human neutrophils.

| Compound | IC$_{50}$ (μM) cytochrome c |
|---|---|
| AS148A | 1 |
| AS158A | 0.6 |
| AS158B | 3 |

TABLE 3-continued

Compounds that inhibit Nox2, assayed by cytochrome c reduction in activated human neutrophils.

| Compound | | IC$_{50}$ (µM) cytochrome c |
|---|---|---|
| AS195 | 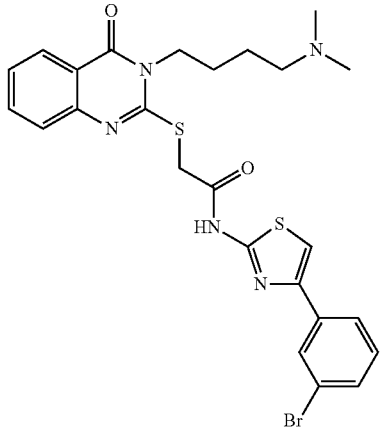 [SMILES: CN(C)CCCCn1c(SCC(=O)Nc2nc(-c3cccc(Br)c3)cs2)nc2ccccc2c1=O] | 1.5 |
| TG6-73 | 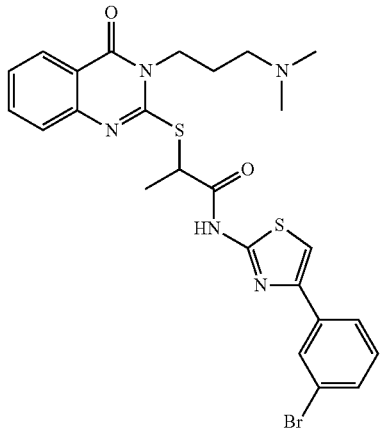 [SMILES: CC(Sc1nc2ccccc2c(=O)n1CCCN(C)C)C(=O)Nc1nc(-c2cccc(Br)c2)cs1] | 2 |

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier, which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more Nox inhibitors can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the Nox inhibitor(s) to carrier and/or other substances may vary from about 0.5 to about 100 wt. % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more Nox inhibitors. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., Nox inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The Nox inhibitors described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the Nox inhibitors can be administered in the same dosage form or in separate dosage forms with one or more other active agents.

Specific examples of compounds that can be adjunctively administered with the Nox inhibitors include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional active agent(s) can be formulated for immediate release, controlled release, or combinations thereof.

Terms

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkyl ester (optionally substituted), aryl ester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH3).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—CH3).

"Alkanoyl" refers to an alkyl as defined above with the indicated number of carbon atoms attached through a carbonyl bride (i.e., —(C═O)alkyl).

"Alkylsulfonyl" refers to an alkyl as defined above with the indicated number of carbon atoms attached through a sulfonyl bridge (i.e., —S(═O)2alkyl) such as mesyl and the like, and "Arylsulfonyl" refers to an aryl attached through a sulfonyl bridge (i.e., —S(═O)2aryl).

"Alkylsulfamoyl" refers to an alkyl as defined above with the indicated number of carbon atoms attached through a sulfamoyl bridge (i.e., —NHS(═O)2alkyl), and an "Arylsulfamoyl" refers to an alkyl attached through a sulfamoyl bridge (i.e., (i.e., —NHS(═O)2aryl).

"Alkylsulfinyl" refers to an alkyl as defined above with the indicated number of carbon atoms attached through a sulfinyl bridge (i.e. —S(═O)alkyl).

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(═O)Rb, —NRaC(═O)NRaNRb, —NRaC(═O)ORb, —NRaSO2Rb, —C(═O)Ra, —C(═O)ORa, —C(═O)NRaRb, —OC(═O)NRaRb, —ORa, —SRa, —SORa, —S(═O)2Ra, —OS(═O)2Ra and —S(═O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

The terms "cycloalkyl" and "cycloalkenyl" refer to mono-, bi-, or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms "halogen" and "halo" refer to fluorine, chlorine, bromine, and iodine.

An unspecified "R" group is a hydrogen, lower alkyl, or aryl all of which may be optionally substituted with one or more substituents. Throughout the specification, groups and substituents thereof may be chosen to provide stable moieties and compounds.

EXPERIMENTAL

Example 1

General Procedure for the Synthesis of Quninazolinone, Quninazolin-2-yl-thioacetamide Analogs

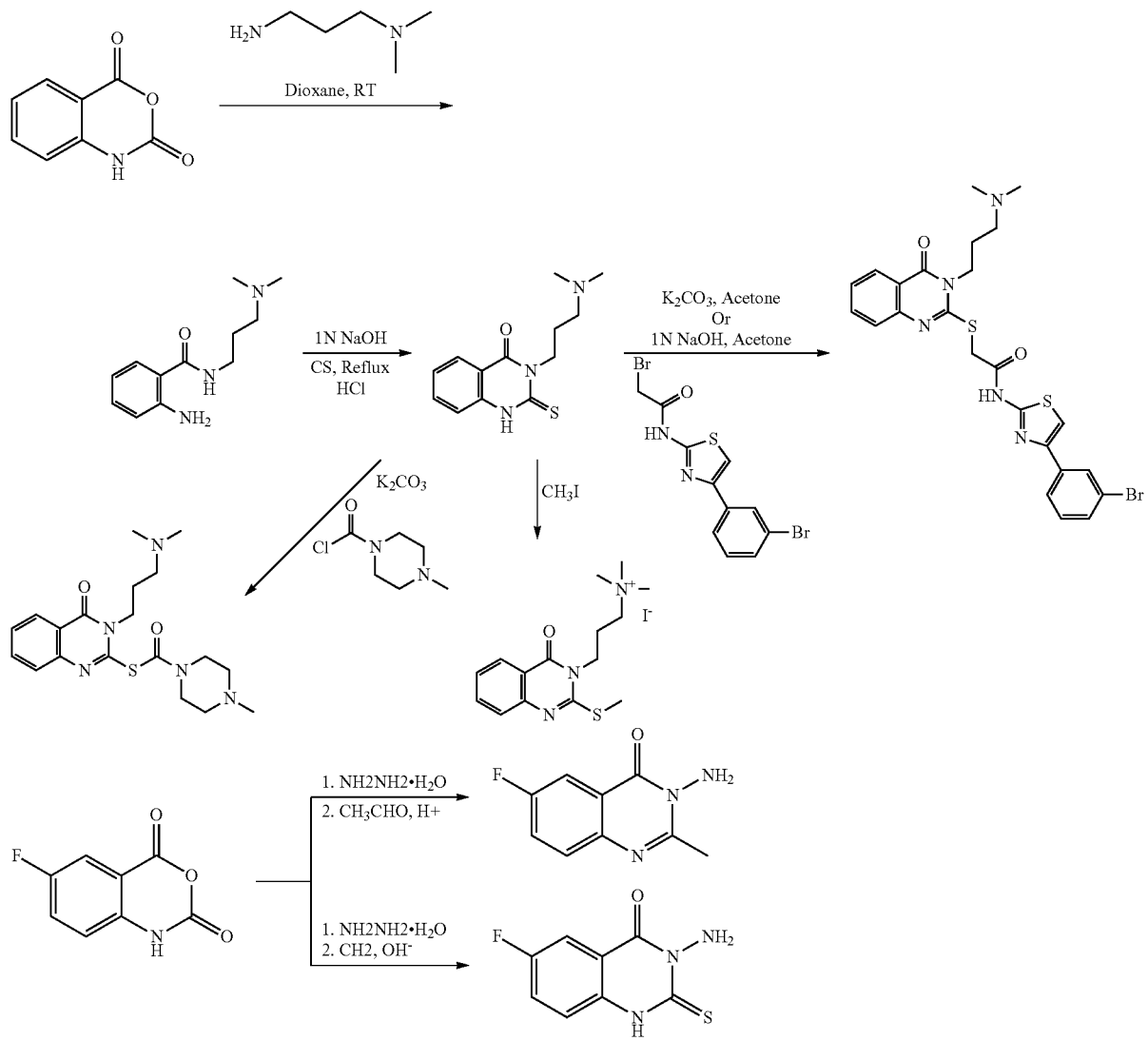

To a solution of isatoic anhydride (2 mmol, 1 eq) in dioxane (4 mL) was added dimethylanimoalkylamine (2 mmol, 1 eq) drop wise, and the resulting solution was stirred at room temperature for 45 min. The dioxane solution was removed under vacuum, and used for next reaction. The product obtained from above reaction (1 eq), was treated with NaOH (1.5 eq) followed by carbon disulfide (1.5 eq) at 80° C. for 6 hrs, to furnish quinazoline compounds up on usual work up and purification. All the derivatives were characterized by $^1$H NMR and LC-MS data. Data for selected compound s is below.

Example TG6-44: $^1$H NMR (400 MHz, DMSO-d$_6$) δ 7.87 (d, J=2.4 Hz, 1H), 7.79 (dd, J=8.8, 2.4 Hz, 1H), 7.40 (d, J=8.8 Hz, 1H), 4.2 (t, J=6.8 Hz, 2H), 3.10 (dd, J=9.6, 5.6 Hz, 2H), 2.69 (s, 6H), 2.0 (m, 2H). LCMS. Cacld. for C13H17ClN3OS (M+H) 298; found 298.

Example TG6-248: $^1$H NMR (400 MHz, DMSO-d$_6$) δ 13.0 (bs, 1H), 10.0 (bs, 1H), 7.66 (m, 2H), 7.44 (dd, J=9.8, 4.4 Hz, 1H), 4.28 (t, J=6.8 Hz, 2H), 3.11 (m, 2H), 2.71 (s, 3H), 2.69 (s, 3H), 2.0 (m, 2H). LCMS. Cacld. for C13H17FN3OS (M+H) 282; found 282.

Example TG6-250: $^1$H NMR (400 MHz, DMSO-d$_6$) δ 13.0 (bs, 1H), 9.9 (bs, 1H), 7.73 (dd, J=10, 8.4 Hz, 1H), 7.33 (dd, J=11, 6.8 Hz, 1H), 4.4 (t, J=6.8 Hz, 2H), 3.10 (t, J=8 Hz, 2H), 2.7 (s, 6H), 2.0 (m, 2H). LCMS. Cacld. for C13H16F2N3OS (M+H) 300; found 300.

Example TG6-53: $^1$H NMR (400 MHz, DMSO-d$_6$) δ 13.1 (bs, 1H), 9.78 (bs, 1H), 7.96 (dd, J=8, 1.2 Hz, 1H), 7.74 (m, 1H), 7.39 (d, J=8 Hz, 1H), 7.33 (t, J=7.2 Hz, 1H), 4.75 (t, J=6.8 Hz, 2H), 3.5 (bd, J=12 Hz, 2H), 3.33 (m, 2H), 2.95 (m, 2H), 1.8 (m, 2H), 1.67 (m, 4H). LCMS. Cacld. for C15H20N3OS (M+H) 290; found 290.

Example TG6-284-2: $^1$H NMR (400 MHz, DMSO-d$_6$) δ 10.0 (bs, 1H), 7.82 (dd, J=9.4, 8.4 Hz, 1H), 6.85 (dd, J=9.4, 6.4 Hz, 1H), 5.95 (m, 1H), 1.52 (d, J=7.2 Hz, 6H). LCMS. Cacld. for C11H11F2N2OS (M+H) 257; found 257.

Example TG7-20-2: $^1$H NMR (400 MHz, DMSO-d$_6$) δ 13.2 (s, 1H), 10.2 (bs, 1H), 7.89 (d, J=2.4 Hz, 1H), 7.80 (dd, J=8.8 Hz, 1H), 7.40 (d, J=8.8 Hz, 1H), 6.93 (d, J=8.8 Hz, 2H), 6.82 (d, J=8.8 Hz, 2H), 4.7 (t, J=6 Hz, 2H), 3.75 (bd, J=11.6 Hz, 2H), 3.66 (s, 3H), 3.60 (bs, 2H), 3.53 (bs, 2H), 3.2 (bs, 2H), 2.96 (t, J=6H, 2H).

Example TG6-295-2: $^1$H NMR (400 MHz, DMSO-d$_6$) δ 7.2 (s, 1H), 6.9 (s, 1H), 3.8 (s, 3H), 3.7 (s, 3H).

Example 2

General Procedure for the Synthesis of Quinazolines: Synthesis of 3-Amino-6,7-dimethoxy-2-thioxo-2,3-dihydroquinazolin-4-one (AS-216a) and Analogs

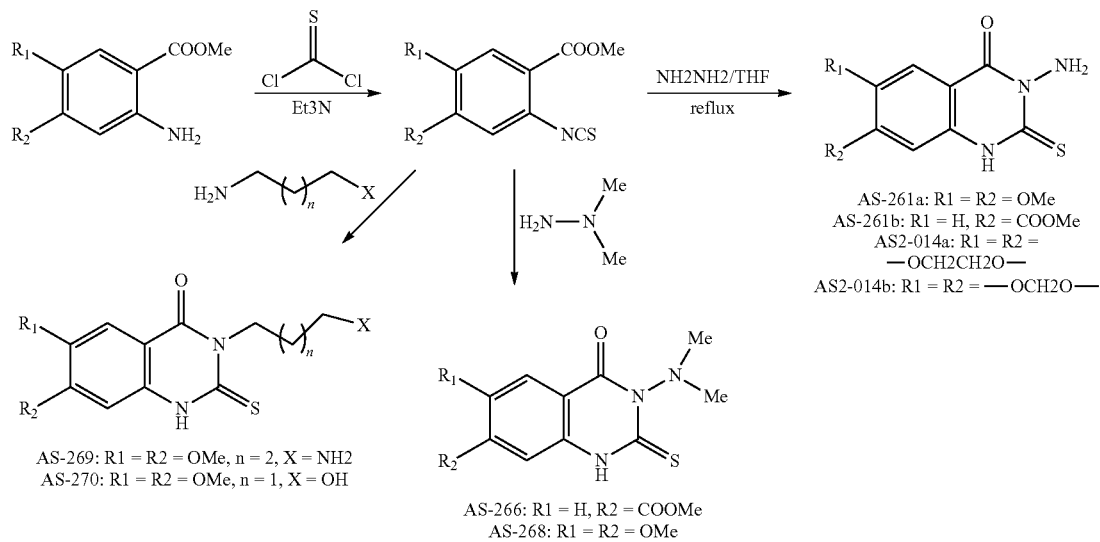

To a solution of thiophosgene (1.1 eq, 1.1 mmol) in EtOAc (10 ml) was added triethyl amine (2.2 eq, 2.2 mmol) at −78° C. over a period of 30 min. After stirring for another 10 min, a solution of methyl 2-aminobenzoate (1.0 eq, 1.0 mmol) in EtOAc (5.0 ml) was added dropwise, then slowly warmed up to room temperature and kept stirring at rt for overnight. The reaction mixture was poured into H$_2$O and extracted with EtOAc (3×10 ml). The combined organic layer was dried over anhydrous Na$_2$SO$_4$, and the solvent was evaporated under reduced pressure. The residue was purified by silica gel column chromatography to obtain methyl 2-isothiocyanatobenzoate derivatives.

To a solution of methyl 2-isothiocyanatobenzoate(s) (1.0 mmol) in THF (5 ml), hydrazine monohydrate (3.1 mmol) was added, followed by stirring under reflux for 2 h. Product (s) was purified by either silica gel column chromatography or recrystallation.

AS-261a: $^1$H NMR (DMSO-d$_6$, 400 MHz): δ 12.97 (s, 1H), 7.31 (s, 1H), 6.94 (s, 1H), 6.34 (s, 2H), 3.85 (s, 6H). Mass, m/z: 254.0 (M+).

AS-266: $^1$H NMR (CDCl$_3$-d, 400 MHz): δ 9.72 (s, 1H), 8.16 (d, J=8.4 Hz, 1H), 7.91 (dd, J=1.6, 6.8 Hz, 1H), 7.75 (s, 1H), 3.99 (s, 3H), 3.09 (s, 6H). Mass, m/z: 280.1 (M+).

AS-268: $^1$H NMR (CDCl$_3$-d, 400 MHz): δ 7.43 (s, 1H), 6.67 (s, 1H), 3.97 (s, 3H), 3.94 (s, 3H), 3.10 (s, 6H). Mass, m/z: 282.1 (M+).

AS2-014a: Mass, m/z: 252.0 (M+).
AS2-014b: Mass, m/z: 238.0 (M+).

Example 3

L-012 Activity Assay for the Nox2/MPO System

Plasma membranes were prepared from human neutrophils. Membranes contain MPO. Membranes were stored at −80 C until use. Membranes are mixed with recombinant, purified cytosolic regulatory proteins (p67Np47 chimera, and constitutively active Rac1 mutant Q61) and FAD, along with varying concentrations of compound, and L-012, which luminesces when it reacts with ROS derived either from Nox2 or from MPO. The reaction is initiated by addition of NADPH and SDS (an artificial activator for Nox2). See Curnutte et al., (1987) J. Biol. Chem. 262: 6450-6452.

Standard methods (CellTiter Kit, Promega) are used to rule out artifacts due to cytotoxicity. Compounds that cause cell lysis within a similar range as their IC50 values, since this will render optimization impossible are eliminated from consideration.

Two assays are used to rule out interference. In one assay, xanthine oxidase replaces the Nox2 and MPO enzymatic system as the source of ROS. See Ritsick et al. (2007) Free Radic Biol Med 43: 31-8. Xanthine was added to start the reaction and LO12 luminescence was recorded. In a control for the luminol assay, exogenous H$_2$O$_2$ is supplied in place of the Nox expressing H$_2$O$_2$-generating cells or enzyme and luminol luminescence is recorded.

Example 3

Cytochrome c Reductase Assay for Superoxide

Isolated human neutrophils, which contain large amounts of Nox2 enzyme, are mixed with superoxide detector cytochrome c. Phorbol 12-myristate 13-acetate (PMA) is added at 1 μM final to stimulate Nox2 activation resulting superoxide production; absorbance at 550 nm is monitored.

Example 4

Activity Assays for MPO

Purified human MPO is mixed with the detector molecule Amplex Red (10-acetyl-3,7-dihydroxyphenoxazine) which increases fluorescence at 590 nm) Hydrogen peroxide is added to initiate the reaction and fluorescence is monitored.

The invention claimed is:

1. A pharmaceutical composition comprising a compound 3-amino-6-fluoro-2-thioxo-2,3-dihydroquinazolin-4(1H)-one or salts thereof.

2. An aqueous biological storage medium comprising a compound of claim 1.

3. The biological storage medium of claim 2, further comprising a salt, an amino acid, a saccharide, a vitamin, or adenosine triphosphate.

* * * * *